United States Patent
De Faveri et al.

(10) Patent No.: US 11,578,043 B2
(45) Date of Patent: Feb. 14, 2023

(54) SALT OF DELMOPINOL

(71) Applicant: Lundbeck Pharmaceuticals Italy S.p.A., Padua (IT)

(72) Inventors: Carla De Faveri, Farra di Soligo (IT); Mariano Stivanello, Schio (IT)

(73) Assignee: Lundbeck Pharmaceuticals Italy S.P.A., Padua (IT)

( * ) Notice: Subject to any disclaimer, the term of this patent is extended or adjusted under 35 U.S.C. 154(b) by 310 days.

(21) Appl. No.: 16/640,843

(22) PCT Filed: Aug. 23, 2018

(86) PCT No.: PCT/EP2018/072764
§ 371 (c)(1),
(2) Date: Feb. 21, 2020

(87) PCT Pub. No.: WO2019/038379
PCT Pub. Date: Feb. 28, 2019

(65) Prior Publication Data
US 2021/0040051 A1  Feb. 11, 2021

(30) Foreign Application Priority Data
Aug. 24, 2017 (IT) .................. 102017000076821

(51) Int. Cl.
| | | |
|---|---|---|
| *C07D 265/30* | (2006.01) | |
| *A23K 20/137* | (2016.01) | |
| *A61K 8/49* | (2006.01) | |
| *A61Q 11/00* | (2006.01) | |

(52) U.S. Cl.
CPC .......... *C07D 265/30* (2013.01); *A23K 20/137* (2016.05); *A61K 8/49* (2013.01); *A61Q 11/00* (2013.01); *C07B 2200/13* (2013.01)

(58) Field of Classification Search
CPC .................................................. C07D 265/30
See application file for complete search history.

(56) References Cited

U.S. PATENT DOCUMENTS

2008/0269222 A1* 10/2008 Lane ..................... A61Q 19/00
514/238.8

FOREIGN PATENT DOCUMENTS

| EP | 0 038 785 A1 | 10/1981 |
|---|---|---|
| WO | 90/14342 A1 | 11/1990 |
| WO | 2007/057681 A1 | 5/2007 |
| WO | 2007/091009 A1 | 8/2007 |
| WO | 2007/099302 A2 | 9/2007 |

OTHER PUBLICATIONS

International Search Report and Written Opinion dated Sep. 27, 2018 in connection with Application No. PCT/EP2018/072764.

* cited by examiner

*Primary Examiner* — Brian J Davis
(74) *Attorney, Agent, or Firm* — Wolf, Greenfield & Sacks, P.C.

(57) ABSTRACT

The present invention relates to a non-hygroscopic salt of the compound 2-(3-(4-propylheptyl)morpholino)ethan-1-ol having the INN name delmopinol. In particular, the invention relates to the citrate salt of delmopinol. The present invention also relates to pharmaceutical compositions comprising the citrate salt of delmopinol depicted below.

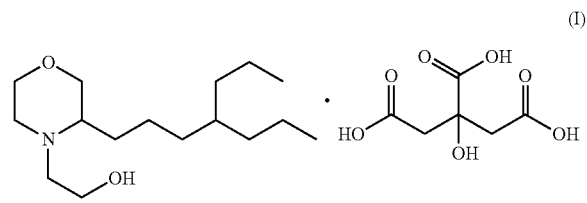

19 Claims, 6 Drawing Sheets

SALT OF DELMOPINOL

CROSS REFERENCE TO RELATED APPLICATIONS

This Application is a National Stage filing under 35 U.S.C. 371 of International Patent Application No. PCT/EP2018/072764, filed Aug. 23, 2018, which claims foreign priority under 35 U.S.C. § 119(a)-(d) or 35 U.S.C. § 365(b) of Italy Application Number 102017000076821, filed Aug. 24, 2017. The entire contents of these applications are incorporated herein by reference in their entirety.

FIELD OF THE INVENTION

The present invention relates to a non-hygroscopic salt of the compound 2-(3-(4-propylheptyl)morpholino)ethan-1-ol having the INN name delmopinol. In particular, the invention relates to the citrate salt of delmopinol. The present invention also relates to pharmaceutical compositions comprising the citrate salt of delmopinol.

BACKGROUND OF THE INVENTION

The compound 2-(3-(4-propylheptyl)morpholino)ethan-1-ol having the INN name delmopinol was disclosed for the first time by Ferrosan in EP0038785 and has the molecular structure depicted below.

Processes for the manufacture of delmopinol have been disclosed e.g. in WO 90/14342, WO 2007/091009 and WO 2007/057681. Delmopinol is commercially available as the HCl salt which is the only known salt of the compound (CAS 98092-92-3).

Delmopinol is used in the treatment of gingivitis, prevention of plaque formation and for oral hygiene in general. Pharmaceutical compositions comprising delmopinol HCl include mouth wash liquids and toothpaste for human use. Other pharmaceutical compositions comprising delmopinol HCl are for use in the maintenance of oral health in animals as described in WO 2007/099302. These compositions include animal chews referring to for example a toy, accessory or foodstuff that is intended for chewing or gnawing by an animal.

There is a need for a new and improved salt of delmopinol for use in the manufacturing of pharmaceutical compositions.

SUMMARY OF THE INVENTION

The present invention relates to a non-hygroscopic salt of delmopinol. In particular, the present invention relates to salt of delmopinol, which is the citrate salt.

The citrate salt of delmopinol is represented by the molecular structure below

In one embodiment, the invention relates to a pharmaceutical composition comprising said citrate salt of delmopinol. Said pharmaceutical composition can be for human or veterinary use.

In one embodiment, the invention relates to said citrate salt of delmopinol for use in the treatment of an oral disease such as gingivitis, or for prevention of plaque formation.

In one embodiment, the invention relates to a method of the treatment of an oral disease such as gingivitis, or for prevention of plaque formation, which method comprises the administration of a therapeutically effective amount of said citrate salt of delmopinol.

In one embodiment, the invention relates to the use of said citrate salt of delmopinol in the manufacture of a medicament for use in the treatment of an oral disease such as gingivitis, or for prevention of plaque formation.

In one embodiment, the invention relates to mouth wash product or a toothpaste comprising said citrate salt of delmopinol.

In one embodiment, the invention relates to an animal chew comprising said citrate salt of delmopinol.

BRIEF DESCRIPTION OF DRAWINGS

The DVS experiments depicted in FIGS. 3 and 4 were performed at 25° C. The first y-axis (left) shows the change in mass (%) and the other y-axis (right) shows the targeted relative humidity (RH) (%), the x-axis shows the time in minutes. The stair-shaped line shows the changes in target RH and the red line shows the changes in relation to mass.

The XRPD diffractograms in FIGS. 5 and 6 were obtained using CuKα1 radiation ($\lambda$=1.5406 Å). The y-axis shows the intensity (counts) and the x-axis shows the 2θ-angles (°).

DEFINITIONS

In the present context, a "non-hygroscopic" salt of delmopinol indicates a salt wherein less than 1.5% moisture is absorbed when the salt is exposed to 95% RH at 25° C. for example when determined by Dynamic Vapor Sorption (DVS) according to the method of Example 4.

In the present context, "1:1 salt" indicates a salt comprising 1 eq of delmopinol and 0.8-1.2 eq of a salt forming acid, such as 1 eq of delmopinol and 0.9-1.1 eq of a salt forming acid, such as 1 eq of delmopinol and 0.95-1.05 eq of a salt forming acid, such as 1 eq of delmopinol and 0.98-1.02 eq of a salt forming acid. In one embodiment, "1:1 salt" indicates a salt comprising 1 eq of delmopinol and 1 eq of a salt forming acid.

Citric acid is a tricarboxylic acid with the formula $C_6H_8O_7$. In the present context, the expressions "citrate salt of delmopinol" and "delmopinol citrate" refers to the 1:1 salt of delmopinol and citric acid.

Figure 1:
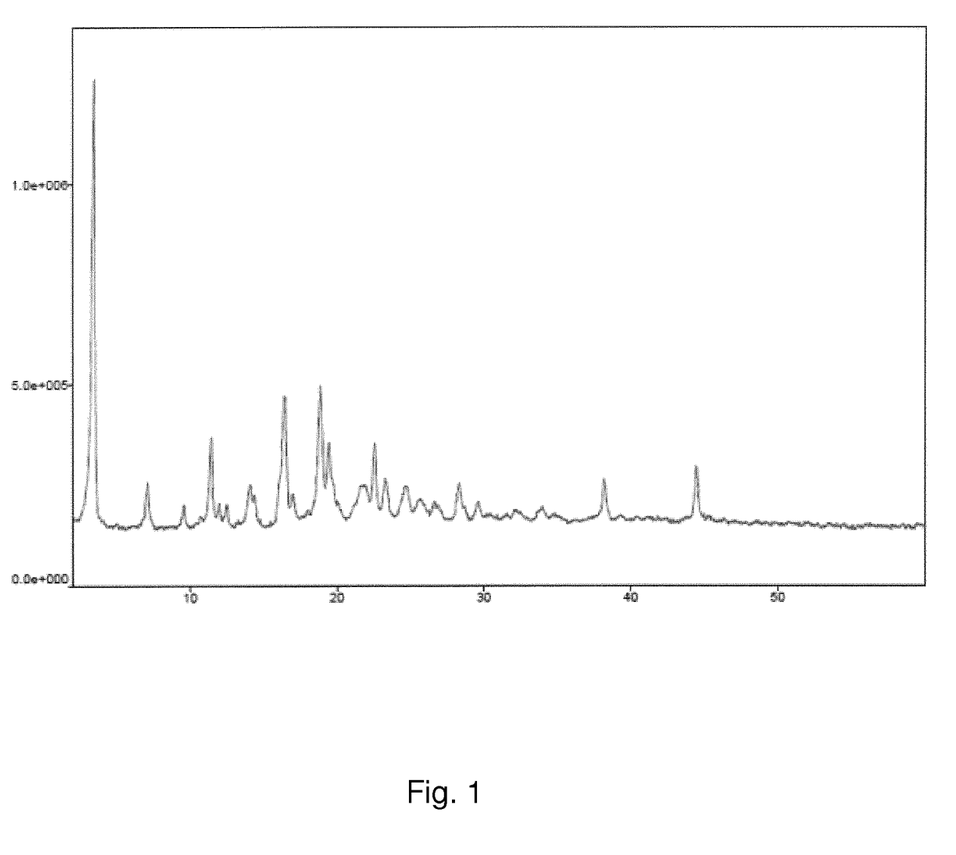
FIG. 1: XRPD pattern of delmopinol citrate. The XRPD diffractogram was obtained using CuKα1 radiation ($\lambda$=1.5406 Å). The y-axis shows the intensity (counts) and the x-axis shows the 2θ-angles (°).

In the present context, by expressions like "delmopinol salt characterized by the XRPD shown in FIG. 1" is meant the crystalline form of a salt of delmopinol having an XRPD substantially similar to FIG. 1, i.e. exhibiting an XRPD pattern with reflections substantially at the angles as exemplified in that Figure and measured under comparable conditions as described herein or by any comparable method.

The term "therapeutically effective amount" means an amount sufficient to cure, alleviate or partially arrest the clinical manifestations of a given disease and its complications in a therapeutic intervention comprising the administration of said compound. An amount adequate to accomplish this is defined as "therapeutically effective amount". It will be understood that determining an appropriate dosage may be achieved using routine experimentation, by constructing a matrix of values and testing different points in the matrix, which is all within the ordinary skills of a trained physician.

In the present context, "treatment" and "treating" refers to the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. In one aspect of the present invention, "treatment" and "treating" refers to prophylactic (preventive) treatment. In another aspect, "treatment" and "treating" refers to (curative) treatment. The patient to be treated is preferably a mammal. In one embodiment, the patient to be treated is a human. In another embodiment, the patient to be treated is a pet such as a cat or a dog.

DETAILED DESCRIPTION OF THE INVENTION

The present invention provides a non-hygroscopic salt of delmopinol. In particular, delmopinol citrate has been identified by the inventors to be non-hygroscopic. The salt is a 1:1 salt of delmopinol and is represented by the molecular structure below.

Figure 4:
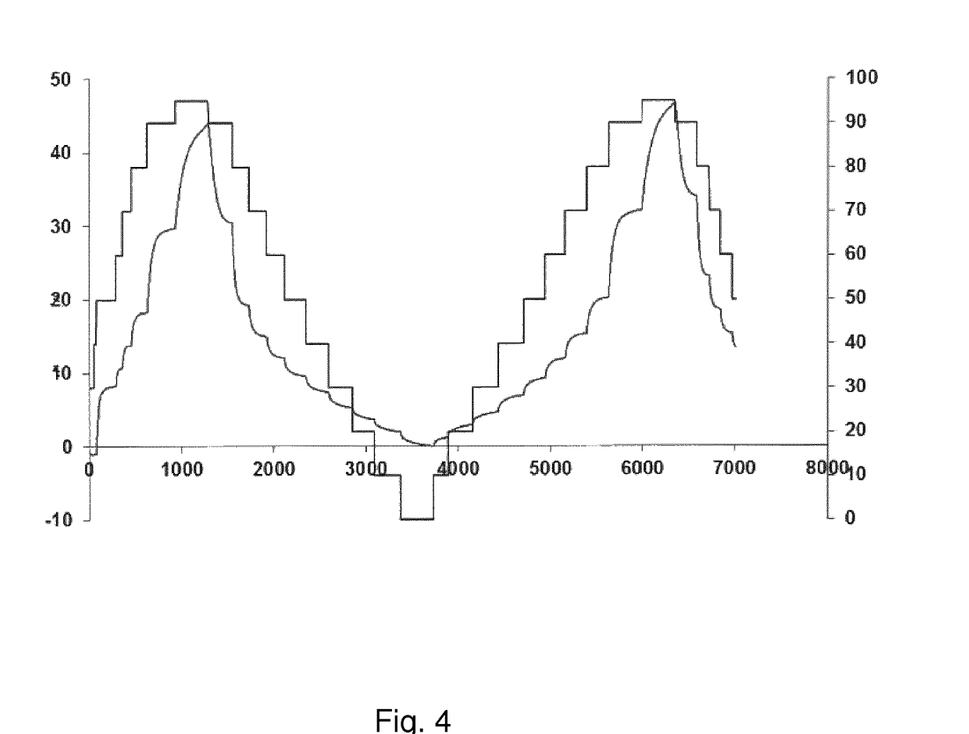
FIG. 4: DVS diagram of the HCl salt of delmopinol.

The inventors have unexpectedly found that the known HCl salt of delmopinol is very hygroscopic. The hygroscopicity of delmopinol HCl is reflected in FIG. 4 depicting the DVS diagram obtained at 25° C. by the method described in Example 4. The diagram shows that the HCl salt starts absorbing water already below 50% humidity and absorbs up till about 45% water when the humidity is increased to 95%. It has also been found that the XRPD of delmopinol HCl after dynamic vapor sorption (DVS) experiments at 95% RH is different from that of the non-exposed material meaning that the change of delmopinol HCl solid state caused by exposure to humidity is irreversible. See FIGS. 5 and 6.

Hygroscopic salts possess the risk of absorbing moisture on storage and must there-fore be packed in containers free of moisture or stored under very dry conditions, which is quite costly. Furthermore, hygroscopic salts are more difficult to handle during processing into for example pharmaceutical products due the risk of absorbing moisture which may influence the quality of the end product.

Figure 3:
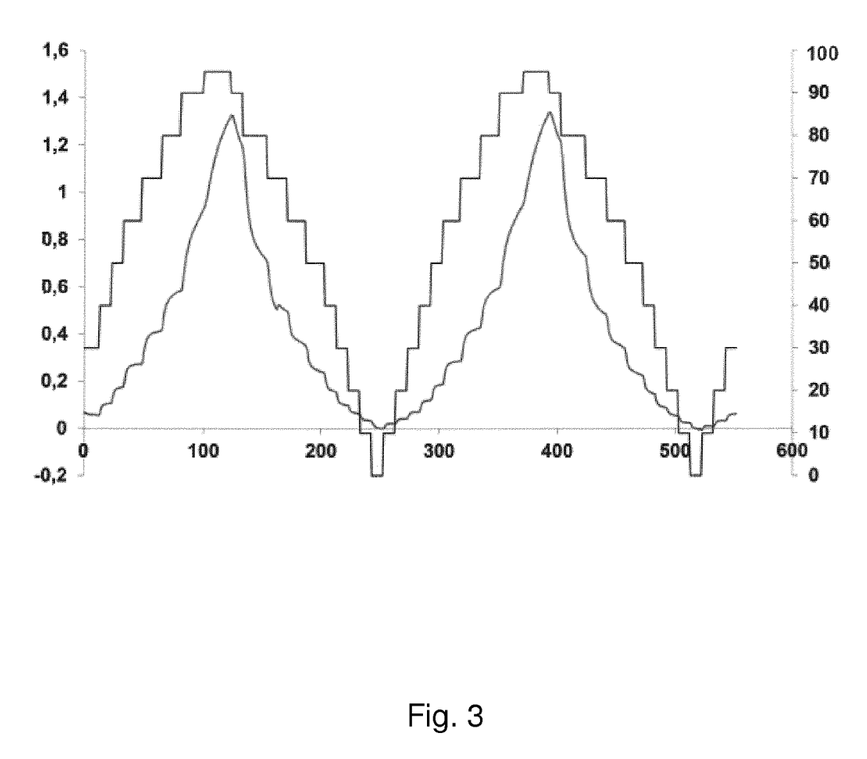
FIG. 3: DVS diagram of delmopinol citrate.

The DVS diagram of delmopinol citrate obtained at 25° C. is depicted in FIG. 3 showing less than 1.5% moisture absorption by increasing the humidity to 95% and thus illustrating that delmopinol citrate is non-hygroscopic.

Moreover, besides being non-hygroscopic, the citrate salt was also found by the inventors to be crystalline. The salt has been characterized by X-ray powder diffractogram (XRPD) according to example 2. The XRPD diffractogram for delmopinol citrate is depicted in FIG. 1, characteristic main reflections are at the following 2θ-angles 3.49, 7.12, 11.47, 14.08, 14.41, 16.41, 18.84, 19.43, 22.55, 24.68, 38.19 and 44.46 (±0.1°2θ).

The present invention also relates to pharmaceutical compositions comprising delmopinol citrate. The pharmaceutical composition may further comprise at least one pharmaceutically acceptable excipient, carrier and/or diluent. Methods for the preparation of pharmaceutical compositions such as liquid pharmaceutical compositions are well known in the art. See, e.g., Remington: The Science and Practice of Pharmacy, 21$^{st}$ ed., Lippincott Williams & Wilkins (2005).

The pharmaceutical compositions can be for human use or for veterinary use. Pharmaceutical compositions comprising delmopinol obtained according to the present invention are intended for local administration in the oral cavity.

The pharmaceutical composition for human use is preferably a liquid composition comprising delmopinol citrate, in a therapeutically effective amount. The pharmaceutical composition can for example be a mouth wash product or a toothpaste. It is envisaged that a pharmaceutical composition for human use comprising delmopinol citrate may be used for treatment of oral diseases such as gingivitis or for prevention of plaque formation. In one embodiment, the composition may be used for general oral hygiene. Preferably, the pharmaceutical composition for human use comprising delmopinol citrate is a liquid composition comprising delmopinol in a concentration of 0.1-0.5%, such as about 0.1%, 0.2%, 0.3%, 0.4% or 0.5%, preferably about 0.2%. Said pharmaceutical composition is preferably a mouth wash product or a toothpaste.

Pharmaceutical compositions for veterinary use comprising delmopinol have been described in WO 2007/099302. In one embodiment, a pharmaceutical composition for veterinary use is an animal chew wherein the term chew is given its normal meaning in the art and refers to any toy, accessory or foodstuff that is intended for chewing or gnawing by an animal (WO 2007/099302). Preferably, the pharmaceutical composition for veterinary use is for use in the treatment of a pet such as a cat or a dog, most preferably a dog. Further variations of compositions for veterinary use comprising delmopinol have been disclosed in WO 2007/099302 which is incorporated herein by reference.

In one embodiment, the invention relates to a mouth wash product or a toothpaste comprising delmopinol citrate.

In one embodiment, the invention relates to an animal chew comprising delmopinol citrate. In a particular embodiment, said animal chew is for use in the treatment of a dog.

In one embodiment, the invention relates to delmopinol citrate, for use in the treatment oral diseases such as gingivitis, or for prevention of plaque formation.

In particular, it is envisaged that a pharmaceutical composition comprising delmopinol citrate may be used for treatment of gingivitis, for prevention of plaque formation and/or for general oral hygiene. In one embodiment, the invention relates to a mouth wash product or a toothpaste comprising delmopinol citrate obtained by the process of the invention.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

Embodiments According to the Invention

In the following, embodiments of the invention are disclosed. The first embodiment is denoted E1, the second embodiment is denoted E2 and so forth.

E1. A salt of delmopinol which is the citrate salt.
E2. The salt of delmopinol according to embodiment 1, represented by the formula E3. The salt of delmopinol according to any of embodiments 1-2, wherein said salt comprises 1 eq of delmopinol and 0.8-1.2 eq of a citric acid, such as 1 eq of delmopinol and 0.9-1.1 eq of citric acid, such as 1 eq of delmopinol and 0.95-1.05 eq of citric acid, such as 1 eq of delmopinol and 0.98-1.02 eq of a citric acid, such as 1 eq of delmopinol and 1 eq of citric acid.
E4. The salt of delmopinol according to any of embodiments 1-3, which salt is crystalline.
E5. The salt of delmopinol according to embodiment 4, which crystal form is characterized by an XRPD obtained using $CuK_{\alpha 1}$ radiation ($\lambda=1.5406$ Å) showing peaks at the following 2θ-angles: 3.49, 11.47, 16.41 and 18.84 (±0.1°2θ).
E6. The salt of delmopinol according to embodiment 4, which crystal form is characterized by an XRPD obtained using CuKα1 radiation ($\lambda=1.5406$ Å) showing peaks at the following 2θ-angles: 3.49, 7.12, 11.47, 14.08, 14.41, 16.41, 18.84, 19.43, 22.55, 24.68, 38.19 and 44.46 (±0.1°2θ).
E7. The salt of delmopinol according to any of embodiments 4-6, which crystal form is characterized by an XRPD obtained using $CuK_{\alpha 1}$ radiation ($\lambda=1.5406$ Å) as depicted in FIG. 1.
E8. The salt of delmopinol according to any of embodiments 4-7, which crystal form is characterized by having a DSC trace showing an endotherm with peak at about 108-111° C.
E9. The salt of delmopinol according to any of embodiments 1-8, wherein less than 1.5% moisture is absorbed when said salt is exposed to 95% RH at 25° C.
E10. The salt according to any of embodiments 1-8, wherein less than 1.5% moisture is absorbed when said salt is exposed to 95% RH at 25° C., when determined by Dynamic Vapor Sorption (DVS).
E11. The salt according to any of embodiments 1-8, wherein less than 1.5% moisture is absorbed when said salt is exposed to 95% RH at 25° C., when determined by Dynamic Vapor Sorption (DVS) according to the method of Example 4.
E12. A salt of delmopinol according to any of embodiments 1-11 for use as a medicament.
E13. A salt of delmopinol according to any of embodiments 1-11 for use in therapy.
E14. A pharmaceutical composition comprising a salt of delmopinol according to any of embodiments 1-11 and at least one pharmaceutically acceptable excipient, carrier and/or diluent.
E15. The pharmaceutical composition according to embodiment 14, wherein said pharmaceutical composition is for human use.
E16. The pharmaceutical composition according to embodiment 15, wherein said pharmaceutical composition is a mouth wash product or a toothpaste.
E17. The pharmaceutical composition according to embodiment 14, wherein said pharmaceutical composition is for veterinary use.
E18. The pharmaceutical composition according to embodiment 17, wherein said pharmaceutical composition is an animal chew.
E19. A mouth wash product or a toothpaste comprising a salt of delmopinol according to any of embodiments 1-11.
E20. An animal chew comprising a salt of delmopinol according to any of embodiments 1-11.
E21. A salt of delmopinol according to any of embodiments 1-11 for use in the treatment of an oral disease such as gingivitis, or for prevention of plaque formation.

E22. A method of the treatment of an oral disease such as gingivitis, or for prevention of plaque formation, which method comprises the administration of a therapeutically effective amount of a salt of delmopinol according to any of embodiments 1-11.

E23. Use of a salt of delmopinol according to any of embodiments 1-11 in the manufacture of a medicament for use in the treatment of an oral disease such as gingivitis, or for prevention of plaque formation.

EXAMPLES

The invention will be illustrated by the following non-limiting examples.

Example 1: Preparation of Delmopinol Citrate

1a: Precipitation from Isopropyl Acetate/THF

Anhydrous citric acid (14.2 g) was added portion-wise at 20-25° C. to a solution of delmopinol (20 g) in isopropyl acetate (150 ml). The suspension was diluted with THF (25 ml) and then stirred overnight. The solid was filtered, washed with isopropyl acetate and dried under vacuum giving 32.4 g of delmopinol citrate.

1b: Precipitation from Ethyl Acetate

To a mixture of anhydrous citric acid (14.2 g) in ethyl acetate (87.5 ml) was added at 20-25° C. a solution of delmopinol (20 g) in ethyl acetate (87.5 ml). The mixture was stirred overnight. The solid was filtered, washed with ethyl acetate and dried under vacuum obtaining 32.2 g of delmopinol citrate.

1c: Precipitation from Isopropanol

To a solution of citric acid monohydrate (15.5 g) in isopropanol (140 ml) was added in one hour at T=45° C. a solution of delmopinol (20 g) in isopropanol (40 ml). The mixture was cooled and seeded. The suspension was stirred at 20° C. overnight. The solid was filtered, washed with isopropanol and dried under vacuum obtaining 30.2 g of delmopinol citrate.

1d: Precipitation from Denatured Ethanol

The procedure reported in 1c was repeated using ethanol denatured with tolu-ene/methanol. Yield: 28.3 g of delmopinol citrate.

1e: Precipitation from Isopropanol/Ethyl Acetate

A solution of delmopinol (20 g) in ethyl acetate (80 ml) was added at room temperature to a solution of anhydrous citric acid (14.2 g) in isopropanol (100 ml). The suspension was stirred overnight. The solid was filtered, washed with ethyl acetate and dried under vacuum yielding 30.7 g of delmopinol citrate.

1f: Precipitation from Isopropanol/Ethyl Acetate

Citric acid monohydrate (185.8 g) was dissolved in isopropanol (1200 ml). A solution of delmopinol (240 g) in ethyl acetate (960 ml) was then added over 2 hours at 20-25° C. The precipitation was initiated by seeding. The mixture was kept under stirring overnight. The solid was isolated by filtration, washed with ethyl acetate (240 ml) and dried under vacuum obtaining 351.9 g of delmopinol citrate.

Example 2: XRPD Characterization

X-Ray powder diffractograms (XRPD) of delmopinol citrate were measured on a Rigaku SmartLab 3 KW (CBO Unit), high resolution theta—theta goniometer using a CuKα1 radiation (λ=1.5406 Å). The samples were measured in reflection mode in the 2 θ-range 2-60° using a D/tex-Ultra 250 detector. The XRPD pattern for delmopinol citrate is shown in FIG. 1. Characteristic main reflections are at the following 2θ-angles: 3.49, 7.12, 11.47, 14.08, 14.41, 16.41, 18.84, 19.43, 22.55, 24.68, 38.19 and 44.46.

Figure 5:
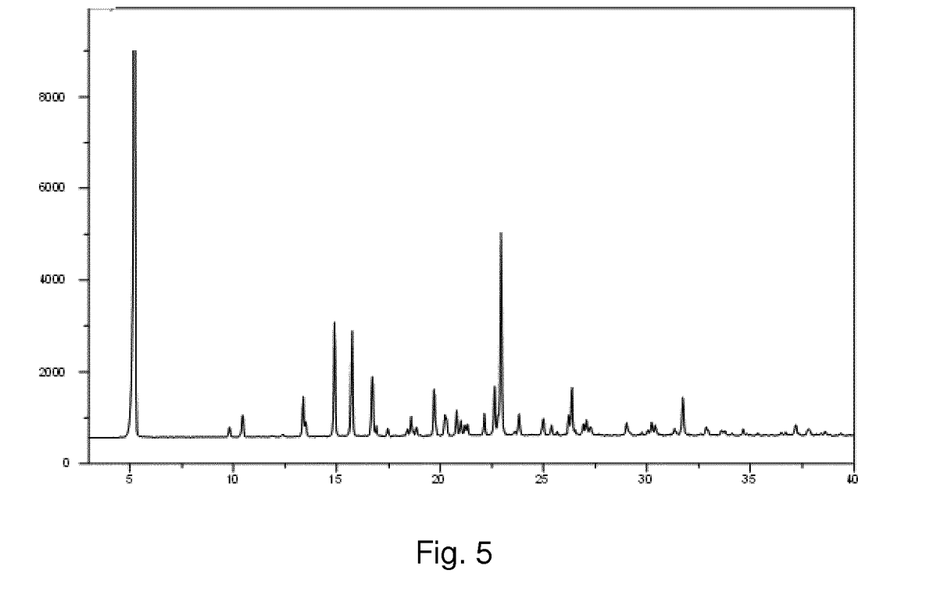
FIG. 5: XRPD pattern of delmopinol HCl before DVS.
Figure 6:
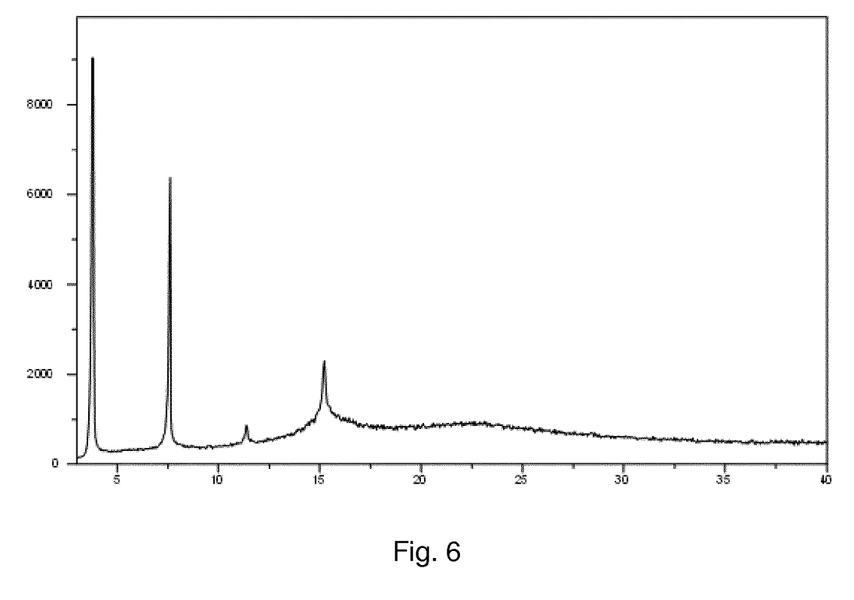
FIG. 6: XRPD pattern of delmopinol HCl after DVS.

XRPD patterns for delmopinol HCl before and after DVS are shown in FIGS. 5 and 6. These diffractograms were obtained on another instrument.

Example 3: Thermal Analysis

The Differential Scanning calorimetry (DSC) measurement of delmopinol citrate were performed using equipment TA-Instruments DSC-Q2000. About 2 mg of sample was heated at 10° C./min under nitrogen flow in a closed pan with a pinhole in the lid.

Figure 2:
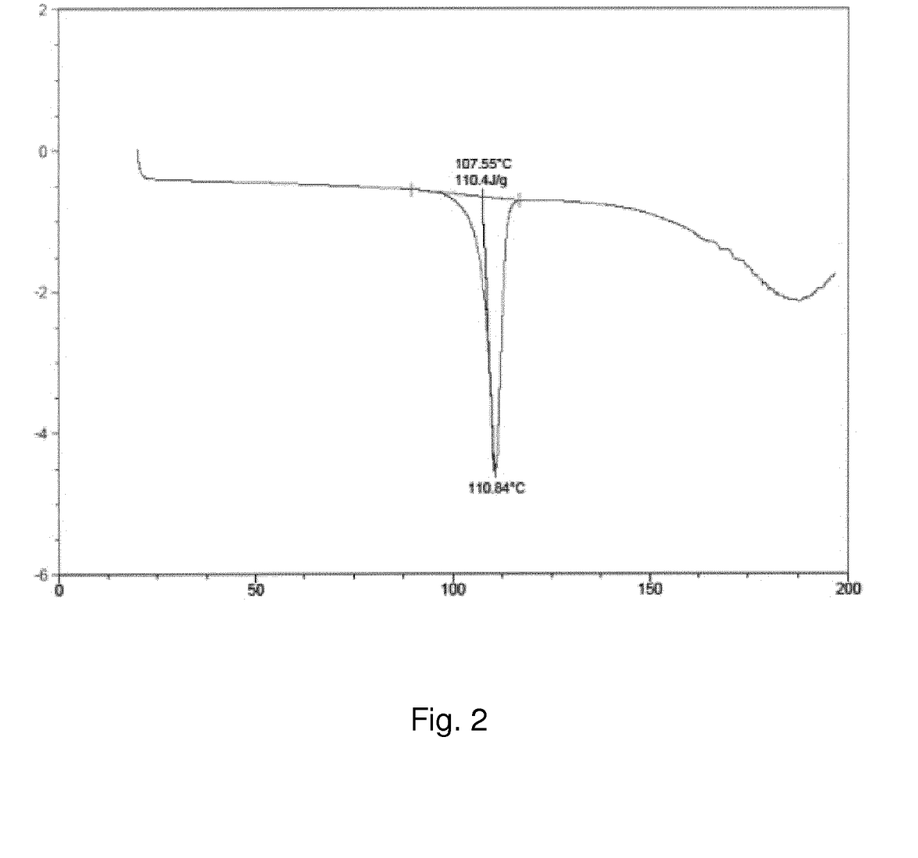
FIG. 2: DSC thermogram of delmopinol citrate. The X axis shows the temperature (° C.), the y-axis shows the DSC heat flow (W/g).

A DSC thermogram of delmopinol citrate is shown in FIG. 2. The compound has an endotherm peak at 110.8° C. with onset at 107.6° C.

Example 4: DVS Experiments

Dynamic Vapour Sorption (DVS) experiments were performed for delmopinol HCl and delmopinol citrate using a SMS DVS Advantage 01 changing the relative humidity from 30% RH up to 95% RH in steps of 10% RH.

The HCl salt of delmopinol absorbs nearly about 45% water when the humidity is increased to 95% while the citrate salt of delmopinol absorbs less than 1.5% moisture when increasing the humidity to 95%.

DVS diagrams for delmopinol citrate and HCl salts are shown in FIGS. 3 and 4, respectively.

The invention claimed is:

1. A citrate salt of delmopinol wherein less than 1.5% moisture is absorbed when said citrate salt is exposed to 95% RH at 25° C.

2. A crystalline citrate salt form of delmopinol characterized by an x-ray powder diffraction (XRPD) spectrum obtained using CuKα1 radiation (λ=1.5406 Å) showing peaks at the following 2θ-angles: 3.49, 11.47, 16.41 and 18.84(±0.1°2θ).

3. The crystalline citrate salt form of delmopinol according to claim 2 characterized by an x-ray powder diffraction (XRPD) spectrum obtained using CuKα1 radiation (λ=1.5406 Å) showing peaks at the following 2θ-angles: 3.49, 7.12, 11.47, 14.08, 14.41, 16.41, 18.84, 19.43, 22.55, 24.68, 38.19 and 44.46 (±0.1°2θ).

4. A crystalline citrate salt of delmopinol characterized by having a Differential Scanning Calorimetry (DSC) trace showing an endotherm with peak at about 108-111° C.

5. A pharmaceutical composition comprising a citrate salt of delmopinol according to claim 1 and at least one pharmaceutically acceptable excipient, carrier and/or diluent.

6. A mouth wash product or a toothpaste comprising a citrate salt of delmopinol according to claim 1.

7. An animal chew comprising a citrate salt of delmopinol according to claim 1.

8. A method for the treatment of an oral disease, or for prevention of plaque formation, in a subject, comprising administering to the subject a citrate salt of delmopinol according to claim 1.

9. A pharmaceutical composition comprising a crystalline citrate salt form of delmopinol according to claim 2 and at least one pharmaceutically acceptable excipient, carrier and/or diluent.

10. A mouth wash product or a toothpaste comprising a crystalline citrate salt form of delmopinol according to claim 2.

11. An animal chew comprising a crystalline citrate salt form of delmopinol according to claim 2.

12. A method for the treatment of an oral disease, or for prevention of plaque formation, in a subject, comprising administering to the subject a crystalline citrate salt form of delmopinol according to claim 2.

13. A pharmaceutical composition comprising a crystalline citrate salt of delmopinol according to claim 4 and at least one pharmaceutically acceptable excipient, carrier and/or diluent.

14. A mouth wash product or a toothpaste comprising a crystalline citrate salt form of delmopinol according to claim 4.

15. An animal chew comprising a crystalline citrate salt of delmopinol according to claim 4.

16. A method for the treatment of an oral disease, or for prevention of plaque formation, in a subject, comprising administering to the subject a crystalline citrate salt of delmopinol according to claim 4.

17. The method of claim 8, wherein the oral disease is gingivitis.

18. The method of claim 12, wherein the oral disease is gingivitis.

19. The method of claim 16, wherein the oral disease is gingivitis.

* * * * *